(12) United States Patent
Rampal et al.

(10) Patent No.: US 6,673,369 B2
(45) Date of Patent: Jan. 6, 2004

(54) CONTROLLED RELEASE FORMULATION

(75) Inventors: Ashok Rampal, Punjab (IN); Rajeev S. Raghuvanshi, New Delhi (IN); Manoj Kumar, Haryana (IN)

(73) Assignee: Ranbaxy Laboratories Limited, Delhi (IN)

( * ) Notice: Subject to any disclaimer, the term of this patent is extended or adjusted under 35 U.S.C. 154(b) by 4 days.

(21) Appl. No.: 10/054,077

(22) Filed: Jan. 22, 2002

(65) Prior Publication Data

US 2003/0175341 A1 Sep. 18, 2003

(51) Int. Cl.$^7$ .............................. A61K 9/22; A61K 9/14
(52) U.S. Cl. .................. 424/468; 424/480; 424/481; 424/488
(58) Field of Search ................. 424/472, 464, 424/454, 485, 465

(56) References Cited

U.S. PATENT DOCUMENTS

| 4,076,804 | A |   | 2/1978  | Sisinger et al. ............. 424/181 |
| 4,119,723 | A |   | 10/1978 | Wyburn-Mason ........... 424/273 |
| 4,176,180 | A |   | 11/1979 | Barbier ....................... 434/181 |
| 4,389,393 | A |   | 6/1983  | Schor et al. ................. 424/19 |
| 4,571,333 | A |   | 2/1986  | Hsiao et al. ................. 424/22 |
| 5,009,897 | A |   | 4/1991  | Brinker et al. .............. 424/469 |
| 5,200,193 | A |   | 4/1993  | Radebaugh et al. ........ 424/468 |
| 5,705,190 | A |   | 1/1998  | Broad et al. ................ 424/465 |
| 5,885,615 | A | * | 3/1999  | Chouinard et al. ......... 424/465 |
| 6,010,718 | A |   | 1/2000  | Al-Razzak et al. ......... 424/464 |
| 6,068,859 | A | * | 5/2000  | Curatolo et al. ............ 424/490 |
| 6,245,351 | B1 | * | 6/2001  | Nara et al. .................. 424/461 |
| 6,261,601 | B1 |   | 7/2001  | Talwar et al. ............... 424/469 |

FOREIGN PATENT DOCUMENTS

| WO | WO 97/22335  |   | 6/1997 | ................. 9/20 |
| WO | WO 00/07570  |   | 2/2000 | ................. 9/20 |
| WO | WO 00/15198  | * | 3/2000 | ........... A61K/9/22 |
| WO | WO 01/52833  |   | 7/2000 | ................. 31/19 |
| WO | WO 00/48607  |   | 8/2000 | ................. 31/70 |
| WO | WO 02/17885  |   | 3/2002 | ................. 9/20 |

* cited by examiner

*Primary Examiner*—Carlos Azpuru
*Assistant Examiner*—Micah Paul Young
(74) *Attorney, Agent, or Firm*—Jayadeep R. Deshmukh, Esq.; George E. Heibel; William Hare, Esq.

(57) ABSTRACT

The present invention relates to a controlled release pharmaceutical composition comprising amounts ranging from about 0.1 to about 4.5% w/w, of one or more of rate controlling cellulosic ether polymers.

27 Claims, No Drawings

CONTROLLED RELEASE FORMULATION

FIELD OF THE INVENTION

The present invention relates to a controlled release pharmaceutical composition comprising amounts ranging from about 0.1 to about 4.5% w/w, of one or more of rate controlling cellulosic ether polymers.

BACKGROUND OF THE INVENTION

It is well known to those skilled in the art that controlled release formulations which are effective in maintaining therapeutic blood levels over extended periods to time result in optimal therapy. They not only reduce the frequency of dosing for enhanced patient convenience and compliance, but they also reduce the severity and frequency of side effects, as they maintain substantially constant blood levels and avoid fluctuations associated with conventional immediate release formulations administered three to four times a day. It is however very difficult to develop controlled release formulations of high dose drugs due to the unacceptably large sizes of the finished dosage form.

In an effort to overcome the problem of size and patient compliance, Abbott has marketed its clarithromycin extended release tablets "Biaxin XL™" as two 500 mg strength tablets to be administered together once a day. Each 500 mg strength tablet weighs around 1000 mg. In their U.S. Pat. No. 6,010,718 Abbott have claimed formulations containing 5%–50% by weight of total polymer. The specification and examples of this patent discloses preferred formulations containing 10%–20% by weight of rate controlling polymer in the formulation in addition to other excipients. The formulation disclosed in this patent has a total tablet weight of about 1000 mg for a tablet containing 500 mg clarithromycin. A tablet containing 1000 mg drug when made in accordance with this invention would therefore be unacceptably large at 2000 mg.

U.S. Pat. No. 5,705,190 describes controlled release compositions for poorly soluble basic drugs comprising a water soluble alginate salt, a complex salt of alginic acid and an organic carboxylic acid to facilitate dissolution of the basic drug at a high pH. The examples disclosed in this patent describe formulations containing 10–20% w/w of rate controlling polymer. The total tablet weight of each tablet containing 500 mg drug as described in the examples of this invention is more than 900 mg, as substantial amounts of polymers are required for controlling the rate of drug release. A single tablet containing 1000 mg drug, when made according to this invention would weigh at least 1800 mg. This would be unacceptably large for human consumption.

U.S. Pat. No. 4,389,393 describes sustained release therapeutic composition using less than about one third of the weight of the solid unit dosage form, of hydroxypropyl methyl cellulose or a mixture of hydroxypropyl methylcellulose with certain other rate controlling polymers. In the specification of this patent, the inventors disclose that they have been able to achieve sustained release from solid dosage forms containing as little as 5 to about 30 weight percent of these hydroxypropyl methylcelluloses. All the examples disclose compositions containing 9% or more of the rate controlling polymer.

Accordingly, none of the oral controlled drug delivery systems heretofore described is completely satisfactory for the delivery of high dose drugs with low water solubility.

It has now surprisingly been found that high dose drugs with low water solubility when formulated with amounts ranging from about 0.1% to about 4.5% w/w of one or more high viscosity cellulosic ether polymers resulted in extended release formulations which release the drug over an extended period of time.

Clarithromycin when formulated with amounts ranging from 0.1% to about 4.5% w/w of one or more high viscosity hydroxypropyl methylcellulose polymers resulted in extended release formulations wherein the area under the concentration time curve and the maximum plasma concentration are within the interval 0.80–1.25 when compared with two tablets of Biaxin XL® administered together as approved by the United States Food and Drug Administration (US FDA).

The use of the claimed amounts of rate controlling polymers not only ensures a more economical formulation compared to one made using larger amounts of polymers, it also ensures better patient compliance as patients have to take only one tablet instead of two tablets together.

SUMMARY OF THE INVENTION

It is an object of the present invention to provide a controlled release formulation suitable for once daily administration, comprising a pharmaceutically effective amount of at least one drug having a water solubility of less than one part per 30 parts water, and from about 0.1% to about 4.5% w/w of one or more rate controlling high viscosity cellulosic ether polymers.

The present invention may apply also to even less soluble drugs for example up to a solubility of one part in 10,000 parts water.

Although, the invention is particularly suitable for high dose drugs but it can advantageously be used for low dose drugs as well, wherein use of small amounts of polymers will result in a more economical formulation.

It is further object of the present invention to provide a controlled release formulation for once daily administration of high dose drugs with low water solubility, wherein the formulation is of an acceptable size and is convenient for oral administration. The use of small amounts of polymers ensures that total weight of the dosage form is low and a single dosage unit is sufficient to provide therapeutic dosage of the drug even when the dosage form has to carry a high payload of the drug. The present formulation provides obvious benefits with respect to small tablets which are more economical and easier to administer therefore ensuring better patient convenience and thereby patient compliance.

The drugs used in accordance with the present invention may be present at a dosage range of about 100–1500 mg. They include, but are not limited to those belonging to the class of:

Analgesics such as Etodolac, Fenoprofen, Tramadol, Paracetamol, Ibuprofen,

Mefenamic acid, Naproxen etc.

Anthelmintics such as Albendazole, Thiabendazole etc.

Cardiovascular drugs such as Chlorothiazide, Dipyridamole etc.

Antibacterials such as Ciprofloxacin, Erythromycin and its derivatives, Norfloxacin Cefaclor, Cefpodoxime, Cefuroxime, Cefalexin and the like.

Bronchodilators/anti-asthmatics such as Doxyfylline, Zileuton, Theophylline etc.

Gastrointestinal drugs such as Cimetidine and Mesalamine,

Oral Antidiabetics such as Tolbutamide and Tolazamide,

Antiprotozoals such as Tinidazol, Nifuratel, Ornidazole, Secnidazole etc.

Antivirals such as Aciclovir

Antiepileptics such as Carbamazepine, Felbamate, Methoin etc.

The cellulosic ether polymers which are effective in the present invention include, but are not limited to hydroxypropyl methylcellulose, hydroxyethyl cellulose, hydroxypropyl cellulose and carboxy methylcellulose polymers. They are all commercially available in a wide variety of viscosity grades which can be used either alone or in combination with other cellulosic ether polymers.

Hydroxypropylmethyl cellulose polymers are commercially available in different viscosity grades. These include 4000 and 15000 cps viscosity grades of Methocel K i.e. Methocel K4M and Methocel K15M available from the Dow Chemical Co, USA and 4000, 15,000 and 39000 cps viscosity grades of Metalose 90 SH available from Shin Etsu Ltd, Japan, the 5,000, 12,000 and 75,000 cps viscosity grades of Methocel J i.e. Metocel JSM, J12M, J20M and J75M, available from Dow Chemical Co and high viscosity grades of Methocel E available from Dow Chemical Co., USA.

One or more hydroxypropyl methylcelluloses having a viscosity of 4000 cps or more can be used as the sole carrier base material or in admixture with other cellulosic ether polymers of the same or higher viscosity.

Hydroxypropyl celluloses are commercially available in a wide range of viscosity grades under the trade name of Klucel® from Nippon Soda, Japan.

In addition to the drug and rate controlling cellulosic ether polymers, the composition may contain about 6 to 50% w/w of other pharmaceutically acceptable excipients such as fillers, binders, and lubricants.

The composition according to the present invention contains fillers selected from amongst those conventionally used in the art such as celluloses, monosaccharides e.g. lactose and glucose; disaccharides e.g. sucrose; polysaccharides e.g. mannitol; silicic acid, and mixtures thereof. Fillers are preferably present at about 5% to about 15% by weight of the formulation.

The composition according to the present invention may also contain binders selected from amongst those conventionally known in the art such as polyvinyl pyrrolidone, sucrose, low viscosity hydroxypropyl methylcellulose, and the like.

The pharmaceutically acceptable lubricants in accordance to the present invention are selected from amongst talc, calcium stearate, magnesium stearate, polyethylene glycol, colloidal silicon dioxide, sodium stearyl fumarate and mixtures thereof.

According to the present invention, the described pharmaceutical composition can incorporate a high dose medicament. The amount of the drug used in the composition can be as high as 1300 mg and the total weight of the tablet does not exceed 1500 mg. The final tablet weight of a formulation containing 1000 mg drug is preferably 1300 mg. Thus the tablets made in accordance to the present invention are unique as they carry a very high payload of the drug and use very small amounts of polymers for controlling the drug release while maintaining the integrity of the tablet.

The composition made according to the present invention may be formulated as a capsule or a tablet. Most preferably, the composition is a tablet. The tablet may optionally be coated with a thin layer of a film forming polymer or a pharmaceutical excipient.

The composition made in accordance with the present invention are further exemplified and illustrated herein.

EXAMPLE 1

The present example relates to a controlled release tablet formulation of tinidazole made using 2.37% of total rate controlling cellulosic ether polymer (a mixture of hydroxypropyl methylcellulose of viscosity 15,000 cps and 4,000 cps commercially available under the trade name of Methocel K15 MCR® and Methocel K4 MCR®, respectively).

TABLE 1.1

| Ingredients | mg/tablet | Percent w/w of composition |
|---|---|---|
| Tinidazole | 1000.0 | 87.1 |
| Methocel K15 MCR ® | 17.5 | 1.5 |
| Methocel K4 MCR ® | 10.0 | 0.87 |
| Lactose | 50.0 | 4.36 |
| Polyvinylpyrrolidone K30 | 25.0 | 2.18 |
| Talc | 10.0 | 0.87 |
| Colloidal Silicon Dioxide | 5.0 | 0.44 |
| Sodium stearyl fumarate | 31.5 | 2.74 |
| Magnesium stearate | 1.0 | 0.1 |
| Total | 1148.0 | |

The drug was blended with the two polymers and lactose and granulated with a solution of polyvinylpyrrolidone in water. The granules were dried, sized lubricated and compressed to tablets.

The tablets thus obtained were optionally film coated. Drug release from the tablets was tested in USP apparatus 2 at 60 rpm in pH 4.0 acetate buffer.

The results (Table 1.2) show that only 2.37% of rate controlling polymer was able to control the release of the drug over an extended period of time.

TABLE 1.2

| Time (h) | Cumulative Percent drug released |
|---|---|
| 1 | 11 |
| 2 | 19 |
| 4 | 35 |
| 6 | 51 |
| 10 | 76 |

EXAMPLE 2

The present example describes clarithromycin controlled release tablets made using 3.23% of total rate controlling cellulosic ether polymer (a mixture of 4000 and 15000 cps viscosity grade hydroxypropyl methylcellulose)

TABLE 2.1

| Ingredients | mg/tablet | Percent w/w of composition |
|---|---|---|
| Clarithromycin | 1000.0 | 86.1 |
| Methocel K15 MCR ® | 25 | 2.15 |
| Methocel K4 MCR ® | 12.5 | 1.08 |
| Lactose | 50.0 | 4.3 |
| Sodium stearyl fumarate | 20.0 | 1.72 |
| Magnesium stearate | 12.5 | 1.08 |
| Talc | 10.0 | 0.86 |
| Colloidal silicon dioxide | 0.5 | 0.43 |
| Total | 1161.5 | |

Clarithromycin was blended with the two polymers and lactose and wet granulated with water. The granules were dried, sized, lubricated and compressed to tablets.

The tablets thus obtained were optionally film coated. Drug release from the tablets was tested in USP apparatus 2 at 80 rpm in pH 4.0 mixed phosphate buffer. The results obtained showed a controlled release of the drug from the dosage form (Table 2.2).

TABLE 2.2

| Time (h) | Cumulative Percent drug released |
| --- | --- |
| 1 | 20 |
| 2 | 35 |
| 4 | 65 |
| 6 | 83 |
| 8 | 86 |

EXAMPLE 3

Tinidazole controlled release tablets made according to the present example uses 1.2% of total rate controlling cellulosic ether polymer (a mixture of hydroxypropyl methylcellulose of 15,000 and 4,000 cps).

TABLE 3.1

| Ingredients | mg/tablet | Percent w/w of composition |
| --- | --- | --- |
| Tinidazol | 1000.0 | 86.5 |
| Methocel K15 MCR ® | 10.0 | 0.865 |
| Methocel K4 MCR ® | 4.0 | 0.346 |
| Starch 1500 | 75.0 | 6.5 |
| Polyvinylpyrolidone K30 | 15.0 | 1.3 |
| Talc | 10.0 | 0.865 |
| Sodium stearyl fumarate | 31.5 | 2.73 |
| Colloidal silicon dioxide | 5.0 | 0.43 |
| Magnesium stearate | 5.0 | 0.43 |
| Total | 1155.5 | |

The drug was blended with the two polymers and lactose and granulated with a solution of starch 1500 in water. The granules were dried, sized, lubricated and compressed to tablets.

The tablets thus obtained were optionally film coated. Drug release from the tablets was tested in USP apparatus 2 at 60 rpm in pH 4.0 acetate buffer and the results showed a controlled release of the drug from the dosage form as given in Table 3.2.

TABLE 3.2

| Time (h) | Cumulative Percent drug released |
| --- | --- |
| 1 | 18 |
| 2 | 29 |
| 4 | 44 |
| 6 | 56 |
| 10 | 79 |

EXAMPLE 4

The present example describes 500 mg strength clarithromycin controlled release tablets made using 4.1% of total rate controlling polymer (a mixture of 4000 and 15000 cps viscosity grade hydroxypropyl methylcellulose)

TABLE 4.1

| Ingredients | mg/tablet | Percent w/w of composition |
| --- | --- | --- |
| Clarithromycin | 500.0 | 58.82 |
| Methocel K15 MCR ® | 7.0 | 0.82 |

TABLE 4.1-continued

| Ingredients | mg/tablet | Percent w/w of composition |
| --- | --- | --- |
| Methocel K4 MCR ® | 28.0 | 3.29 |
| Lactose | 263.0 | 30.94 |
| PVP 30 | 12.0 | 1.41 |
| Sodium stearyl fumarate | 17.0 | 2.0 |
| Magnesium stearate | 3.0 | 0.35 |
| Talc | 15.0 | 1.76 |
| Aerosil 200 | 5.0 | 0.58 |
| Total | 850.0 | |

The tablets thus obtained were optionally film coated. Drug release from the tablets was tested in USP apparatus 2 at 80 rpm in pH 4.0 mixed phosphate buffer and the results showed a controlled release of the drug from the dosage form as given in Table 4.2.

TABLE 4.2

| Time (h) | Cumulative Percent drug released |
| --- | --- |
| 1 | 19 |
| 2 | 35 |
| 4 | 62 |
| 6 | 83 |
| 8 | 92 |

EXAMPLE 5

A formation was made using a combination of two viscosity grades (4000 cps and 15,000 cps) of HPMC polymer and sodium carboxymethyl cellulose (Sodium CMC). The total amount of rate controlling polymer used was only 2.39%.

TABLE 5.1

| Ingredients | mg/tablet | Percent w/w of composition |
| --- | --- | --- |
| Clarithromycin | 1000.0 | 87.33 |
| Methocel K15 MCR ® | 10.0 | 0.87 |
| Methocel K4 MCR ® | 9.0 | 0.78 |
| Sodium CMC | 8.5 | 0.74 |
| Lactose | 50.0 | 9.36 |
| PVP 30 | 20 | 1.74 |
| Sodium stearyl fumarate | 31.5 | 2.7 |
| Magnesium stearate | 1.0 | 0.08 |
| Talc | 10.0 | 0.87 |
| Aerosil 200 | 5.0 | 0.43 |
| Total | 1145.0 | |

The tablets thus obtained were optionally film coated. Drug release from the tablets was tested in USP apparatus 2 at 80 rpm in pH 4.0 mixed phosphate buffer and the results showed a controlled release of the drug from the dosage form as given in Table 5.2.

TABLE 5.2

| Time (h) | Cumulative Percent drug released |
| --- | --- |
| 1 | 20 |
| 2 | 45 |
| 4 | 77 |
| 8 | 91 |

EXAMPLE 6

A controlled release formulation for clarithromycin was made using sodium carboxymethyl cellulose (Sodium CMC) and hydroxypropyl cellulose as the rate controlling polymers. Only 2.5% of rate controlling polymer was used to control the drug release from the formulation.

TABLE 6.1

| Ingredients | mg/tablet | Percent w/w of composition |
|---|---|---|
| Clarithromycin | 1000.0 | 84.21 |
| Sodium CMC | 20.0 | 1.68 |
| Hydroxypropyl cellulose L | 10.0 | 0.84 |
| Lactose | 90.0 | 7.57 |
| PVP 30 | 20.0 | 1.68 |
| Sodium stearyl fumarate | 31.5 | 2.65 |
| Magnesium stearate | 1.0 | 0.084 |
| Talc | 10.0 | 0.84 |
| Aerosil 200 | 5.0 | 0.42 |
| Total | 1187.5 | |

The tablets thus obtained were optionally film coated. Drug release from the tablets was tested in USP apparatus 2 at 80 rpm in pH 4.0 mixed phosphate buffer and the results showed a controlled release of the drug from the dosage form as given in Table 6.2.

TABLE 6.2

| Time (h) | Cumulative Percent drug released |
|---|---|
| 1 | 20 |
| 2 | 43 |
| 4 | 75 |
| 6 | 88 |
| 8 | 91 |

EXAMPLE 7

Clarithromycin controlled release tablets were formulated using a combination of two viscosity grades (15,000 and 4,000 cps) of the rate controlling polymer hydroxypropyl methylcellulose sold under the trade name of Methocel K 4MCR® and Methocel K15 MCR®. The two polymers together comprised only 1.75% of the total tablet weight.

TABLE 7.1

| Ingredients | Mg/tablet | Percent w/w of composition |
|---|---|---|
| Clarithromycin | 1000.0 | 84.8 |
| Methocel K15 MCR ® | 12.5 | 1.06 |
| Methocel K 4 MCR ® | 8.0 | 0.68 |
| Methocel E 50 ® | 8.0 | 0.68 |
| Lactose | 75.0 | 6.36 |
| Magnesium stearate | 12.5 | 1.06 |
| Talc | 10.0 | 0.85 |
| Colloidal Silicon Dioxide | 5.0 | 0.43 |
| Sodium stearyl fumarate | 20.0 | 1.7 |
| Total | 1179.00 | |

Clarithromycin was blended with the two polymers and lactose and granulated with solution of methocel E50 in water. The granules were dried, sized, mixed with the remaining excipients and compressed to tablets.

The tablets thus obtained were optionally film coated. The drug release from the tablets was in USP apparatus 2 at 80 rpm pH 4.0 mixed phosphate buffer, and the results obtained show that only 1.75% of the rate controlling polymer was surprisingly able to control the release of the drug from the dosage from over an extended period of time (Table 1.2).

TABLE 7.2

| Time (h) | Cumulative Percent drug released |
|---|---|
| 1 | 23 |
| 2 | 38 |
| 4 | 70 |
| 6 | 93 |
| 8 | 99 |

EXAMPLE 8

According to the present example clarithromycin controlled release tablets were made using 2.35% of total rate controlling polymer (a mixture of 4000 and 15000 cps viscosity grade hydroxypropyl methylcellulose)

TABLE 8.1

| Ingredients | Mg/tablet | Percent w/w of composition |
|---|---|---|
| Clarithromycin | 1000.0 | 84.6 |
| Methocel K15 MCR ® | 10.0 | 0.85 |
| Methocel K 4 MCR ® | 17.5 | 1.5 |
| Lactose | 50.0 | 4.2 |
| Polyvinyl pyrrolidone | 25.0 | 2.1 |
| Magnesium stearate | 12.5 | 1.1 |
| Talc | 10.0 | 0.85 |
| Colloidal Silicon Dioxide | 5.0 | 0.40 |
| Sodium stearyl fumarate | 20.0 | 1.70 |
| Total | 1182.0 | |

Clarithromycin was blended with the two polymers and lactose and granulated with a solution of polyvinyl pyrolidone in water. The granules were dried, sized, lubricated and compressed to tablets.

The tablets thus obtained were optionally film coated. Drug release from the tablets was tested in USP apparatus 2 at 80 rpm in pH 4.0 mixed phosphate buffer. The results obtained once again showed that 2.35% of the total rate controlling polymer was able to control the rate of drug release over a period of 10 hours (Table 2.2).

TABLE 8.2

| Time (h) | Cumulative Percent drug released |
|---|---|
| 1 | 23 |
| 2 | 43 |
| 4 | 70 |
| 6 | 88 |
| 8 | 97 |

Pharmacokinetic Study

The formulations made in accordance with Examples 7 and 8 were subjected to bioavailability studies against clarithromycin 500 mg immediate release tablets administered in as BID dosage regimen and commercially available under the trade name Biaxin®.

A randomized, three treatment, three period, three sequence, single dose, crossover bioavailability study on clarithromycin XL 1000 mg tablets of the present invention administered once daily with Biaxin® 500 mg tablet of Abbott Laboratories administered 12 hourly in two doses to healthy, adult, male human subjects.

Values for clarithromycin pharmacokinetic parameters including Cmax, and AUCo-t were calculated. Table 9 summarizes the pharmacokinetic results obtained.

TABLE 9

| Formulation | Cmax (µg/ml) | AUC$_{0-t}$ (µg · hr/ml) |
|---|---|---|
| A | 2.669 | 37.248 |
| B | 3.025 | 33.389 |
| Reference | 3.401 | 37.945 |

Table 10 gives the point estimates of relative bioavailability (Test/Reference ratios) for the two one-sided test procedure from analysis of log transformed AUC (0-t) and Cmax.

TABLE 10

| Formulation comparison | Cmax (µg/ml) | AUC$_{0-t}$ (µg · hr/ml) |
|---|---|---|
| A/R | 78.07 | 94.34 |
| B/R | 92.01 | 88.29 |

A : Formulation made in accordance with Example 8.
B : Formulation made in accordance with Example 7.
Reference: Biaxin ® IR 500 mg tablets administered in a BID dosage regimen.

As can be seen from Tables 9 and 10 above, the two controlled release formulations A and B made in accordance with the present invention show a bioavailability profile similar to the commercially available immediate release Biaxin® formulation administered in a BID dosage regimen.

In the next study, the single tablet formulation made in accordance to Example 8 was subjected to a comparative bioavailability study against the commercially available Biaxin XL® tablets (two controlled release tablets to be administered together once a day).

Table 11 lists the pharmacokinetic parameters for the two clarithromycin XL formulations in healthy male subjects.

TABLE 11

| Formulation comparison | Cmax (µg/ml) | AUC$_{0-t}$ (µg · hr/ml) |
|---|---|---|
| Biaxin XL ® (2 × 500 mg) tablets (Reference) | 3.041 | 42.016 |
| Clarithromycin XL 1000 mg tablets (Test) | 3.032 | 42.210 |

Table 12 gives the point estimates of the relative bioavailability and 90% confidence intervals from log transformed AUC$_{0-t}$ and Cmax.

TABLE 12

| Formulation comparison | Cmax(µg/ml) | AUC$_{0-t}$ (µg · hr/ml) | AUC$_{0-\infty}$ (µg · hr/ml) |
|---|---|---|---|
| Test./Reference | 99.33 | 99.15 | 103.39 |
| 90% confidence interval | 81.5–121.0 | 87–112.9 | 91–114.8 |

The data given above shows that formulation of the present invention containing only 2.35% of a rate controlling polymer can surprisingly produce a bioequivalent formulation (as required by the US FDA guidelines on bioequivalence) to Biaxin XL®, which is made using substantially higher quantities of rate controlling polymers.

While the present invention has been described in terms of its specific embodiments, certain modifications and equivalents will be apparent to those skilled in the art and are intended to be included within the scope of the present invention.

What is claimed is:

1. A controlled release formulation, suitable for once daily administration, comprising a pharmaceutically effective amount of at least one drug having a water solubility of less than one part per 30 parts water, and from about 0.1% to about 4.5% w/w of one or more rate controlling high viscosity cellulosic ether polymers wherein the high viscosity polymer comprises a polymer having a viscosity of at least about 4,000 cps or more.

2. The controlled release formulation of claim 1 wherein the drug comprises from about 10% w/w to about 90% w/w of the composition.

3. The controlled release formulation of claim 1 wherein the drug comprises from about 50% w/w to about 90% w/w of the composition.

4. The controlled release formulation of claim 1 wherein the drug is selected from those belonging to the therapeutic categories of analgesics, anthelmintics, cardiovasculars, antibacterials, bronchodilators, anti-asthmatics, gastrointestinal drugs, antidiabetics, antiprotozoals, antivirals and anti epileptics.

5. The controlled release formulation of claim 1 wherein the drug is selected from the group consisting of etodolac, albendazole, chlorothiazide, ciprofloxacin, erythromycin and its derivative doxyfylline cimetidine, tolbutamide, tinidazol, aciclovir, carbamazepine, and their phamiaccutically acceptable salts and esters.

6. The controlled release formulation of claim 1 wherein the cellulosic ether polymers are selected from amongst hydroxypropyl methylcellulose, hydroxypropylcellulose, carboxy methylcellulose, hydroxy ethylcellulose, sodium carboxy methylcellulose, and mixtures thereof.

7. The controlled release formulation of claim 6 wherein the cellulosic ether polymer is hydroxypropyl methylcellulose either alone or in combination with other cellulosic ether polymers.

8. The controlled release formulation of claim 7 wherein hydroxypropyl methylcellulose has a viscosity of 4000 cps or more.

9. The controlled release formulation of claim 8, wherein the high viscosity hydroxypropyl methylcellulose polymers are selected from amongst those having a viscosity of 4000 cps, 15,000 cps, and mixtures thereof.

10. The controlled release formulation of claim 1 wherein the formulation may additionally contain other pharmaceutically acceptable excipients such as fillers, binders, and lubricants.

11. The controlled release formulation of claim 10 wherein the filler is selected from the group consisting of monosaccharides, disaccharides, polysaccharides, starches, celluloses, and mixtures thereof.

12. The controlled release formulation of claim 10 wherein the filler comprises from about 5% w/w to about 15% w/w of the composition.

13. The controlled release formulation of claim 10 wherein the lubricant is selected form amongst (he group consisting of talc, calcium stearate, magnesium stearate, polyethylene glycol, sodium stearyl fumarate, and mixtures thereof.

14. The controlled release formulation of claim 10 wherein the binder is selected from amongst polyvinyl pyrrolidone, starch, low viscosity grade hydroxypropyl methylcellulose, hydroxyethyl cellulose, and the like.

15. The controlled release formulation of claim 1 wherein the formulation is a tablet or a capsule.

16. The controlled release formulation of claim 15 wherein the formulation is a tablet.

17. The controlled release formulation of claim 15 wherein the tablet is optionally film coated.

18. The controlled release monolithic tablet formulation comprising 100–1300 mg of drug and 0.1% to 4.5% w/w of one or more than one rate controlling cellulosic ether polymer wherein the total tablet weight is not more than 1500 mg and the one or more than one rate controlling polymers have a viscosity of about 4,000 cps or more.

19. The controlled release monolithic tablet formulation of claim 18 comprising about 1000 mg drug wherein the total weight is not more than 1300 mg.

20. The controlled release monolithic tablet formulation of claim 18 wherein the tablet comprises a drug with low solubility in water and 0.1% w/w to 4.5% w/w of one or more than one rate controlling polymer wherein the rate controlling polymers is a cellulose ether polymer.

21. The controlled release tablet formulation of claim 18 wherein the rate controlling polymer is hydroxypropyl methylcellulose of viscosity grades 4000 cps, 15,000 cps, and mixtures thereof.

22. An extended release formulation comprising 1000 mg of clarithromycin and pharmaceutically acceptable excipients, and from about 0.1%, to about 4.5% w/w of one or more rate controlling high viscosity cellulosic ether polymers, wherein the total weight of the dosage unit is not more than 1500 mg wherein the rate controlling polymer has a viscosity of about 4,000 cps or more.

23. An extended release pharmaceutical unit dose composition of 1000 mg of clarithromycin comprising from about 0.1% to about 4.5% weight of a high viscosity hydroxypropyl methylcellulose polymer the rate controlling polymer having a viscosity of about 4,000 cps or more, wherein when ingested orally, the composition provides area under the concentration-time curve and the maximum plasma concentration substantially equivalent to the commercially available daily dose of two 500 mg strength clarithromycin tablets administered together.

24. A unit dose extended release tablet composition comprising 1000 mg of clarithromycin and from about 0.1% to about 4.5% by weight of high viscosity hydroxypropyl methylcellulose polymer the rate controlling polymer having a viscosity of about 4,000 cps or more, wherein the 90% confidence interval of clarithromycin area under the concentration-time curve and maximum plasma concentration is within the interval 0.80–1.25 when compared with commercially available daily dose of two 500 mg strength clarithromycin tablets administered together.

25. The extended release composition of claim 23 wherein the high viscosity hydroxypropyl methylcellulose polymers comprise one or more than one polymer having a viscosity of about 4000 cps or more about 15,000 cps or more, or mixtures thereof.

26. The extended release composition of claim 23 wherein clarithromycin comprises from about 10% to about 90% w/w of the composition.

27. The extended release composition of claim 25 wherein clarithromycin comprises from about 50% w/w to about 90% w/w of the composition.

* * * * *

UNITED STATES PATENT AND TRADEMARK OFFICE
CERTIFICATE OF CORRECTION

PATENT NO.    : 6,673,369 B2
DATED         : January 6, 2004
INVENTOR(S)   : Rampal et al.

It is certified that error appears in the above-identified patent and that said Letters Patent is hereby corrected as shown below:

Column 7,
Line 67, "from" should read -- form --.

Column 10,
Line 58, "(he group" should read -- the group --.

Column 11,
Line 25, "0.1%, to" should read -- 0.1% to --.

Column 12,
Lines 2 and 12, "polymer the" should read -- polymer, the --

Signed and Sealed this

Twenty-seventh Day of July, 2004

JON W. DUDAS
*Acting Director of the United States Patent and Trademark Office*